(12) United States Patent
Du et al.

(10) Patent No.: US 6,875,220 B2
(45) Date of Patent: Apr. 5, 2005

(54) DUAL PROBE

(75) Inventors: Shu Du, Erie, PA (US); Thomas M. Peterson, Erie, PA (US); Tao Song, Erie, PA (US)

(73) Assignee: Cybersonics, Inc., Erie, PA (US)

( * ) Notice: Subject to any disclaimer, the term of this patent is extended or adjusted under 35 U.S.C. 154(b) by 143 days.

(21) Appl. No.: 10/334,486

(22) Filed: Dec. 30, 2002

(65) Prior Publication Data

US 2004/0127925 A1 Jul. 1, 2004

(51) Int. Cl.[7] .................................................. A61B 17/32
(52) U.S. Cl. ........................................ 606/169; 604/22
(58) Field of Search ................................ 606/128, 169; 604/22

(56) References Cited

U.S. PATENT DOCUMENTS

| | | | |
|---|---|---|---|
| 4,178,935 A | * 12/1979 | Gekhman et al. | ........... 606/128 |
| 4,828,052 A | 5/1989 | Duran et al. | |
| 5,160,336 A | * 11/1992 | Favre | .......................... 606/128 |
| 5,414,673 A | 5/1995 | Scherbatskoy | |
| 5,562,169 A | 10/1996 | Barrow | |
| 5,582,247 A | 12/1996 | Brett et al. | |
| 5,676,213 A | 10/1997 | Auzerais et al. | |
| 5,868,756 A | * 2/1999 | Henry et al. | ................. 606/128 |
| 5,899,958 A | 5/1999 | Dowell et al. | |
| 6,214,017 B1 | * 4/2001 | Stoddard et al. | ............ 606/128 |

* cited by examiner

*Primary Examiner*—Anhtuan T. Nguyen
*Assistant Examiner*—Tan-Uyen T. Ho
(74) *Attorney, Agent, or Firm*—Walter A. Hackler

(57) ABSTRACT

A percutaneous surgical instrument for de-bulking calculi or drilling bone includes an actuator for generating vibrations at ultrasonic frequencies and a horn coupled to said actuator for amplifying the actuator vibration. A fixed probe is attached to said horn for engaging the calculi and introducing the ultrasonic frequencies thereto. A floating probe is disposed concentric to and over said fixed probe and slidable thereover. A free mass is disposed between the horn and the floating probe for oscillating therebetween, in response to actuator vibration, for causing low frequency impact with the calculi.

26 Claims, 2 Drawing Sheets

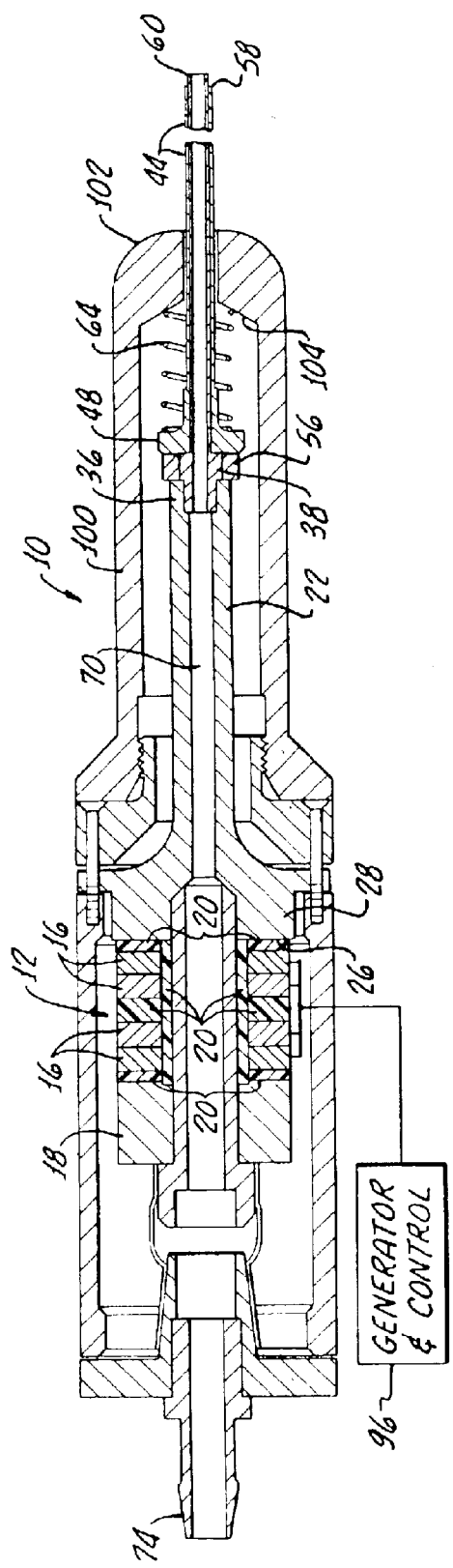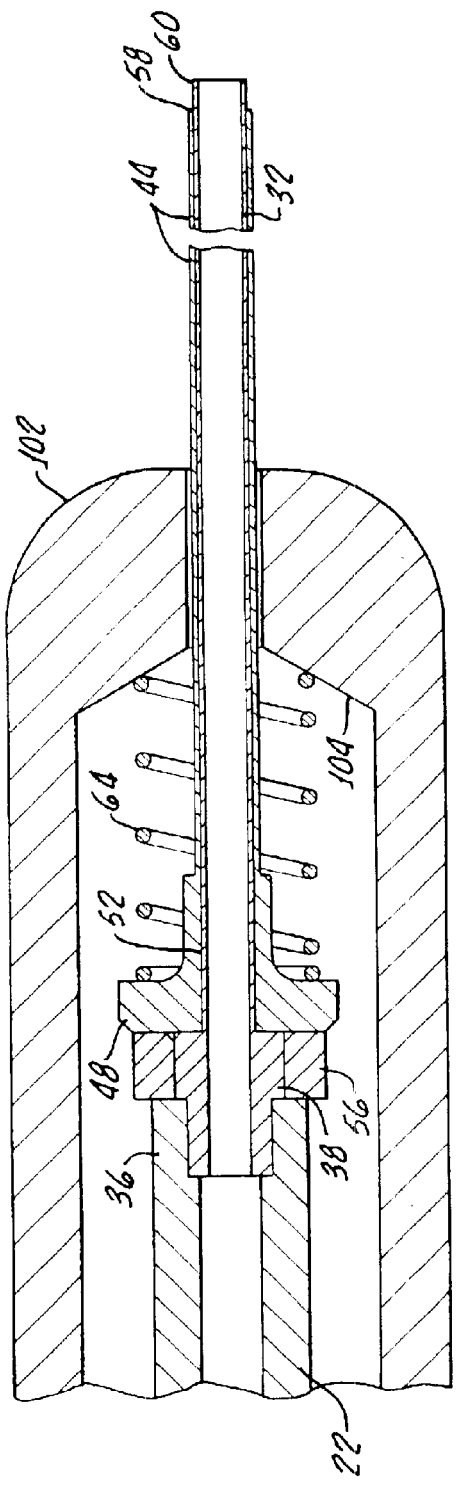

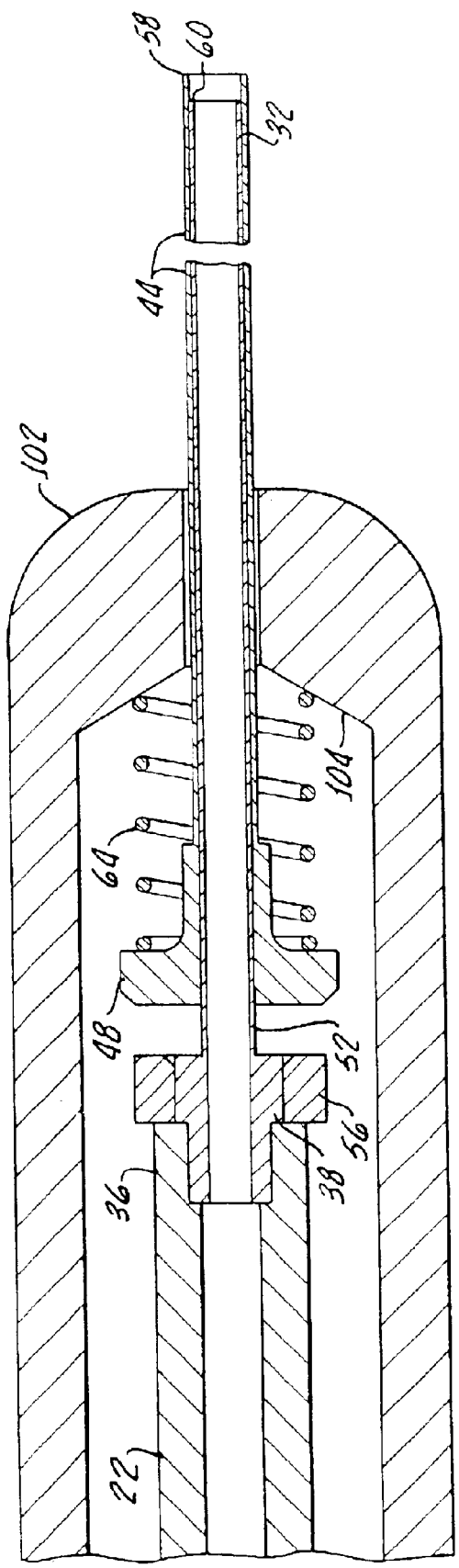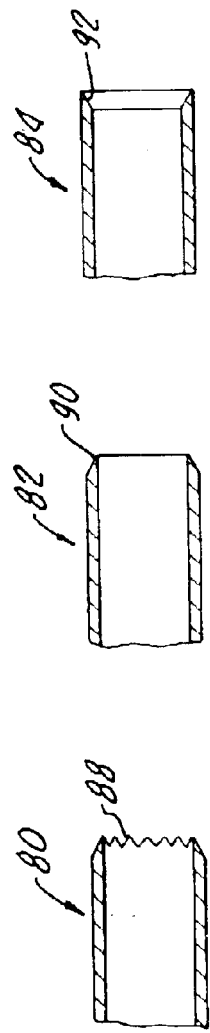

DUAL PROBE

The present invention is generally directed to a surgical instrument for disintegrating and de-bulking calculi or drilling stone, or bone and is more particularly directed to percutaneous surgical instruments for use in urological lithotripsy.

Many people develop calculi within their common bile, urinary, renal, or urethral systems. Such calculi may block ducts and/or cause great pain and therefore must be removed.

Originally, open surgery has been performed wherein multiple incisions are made to approach and remove the calculi. However, this treatment results in a relatively long recovery period and has long fallen into disfavor.

Presently, such calculi are destroyed in situ after which the fragmented calculi can be naturally evacuated. Various methods of de-bulking such calculi are known in the art. Instruments currently in use are typically ultrasonic fixed probe devices or pneumatic impacting probes that operate at fixed low frequencies.

Fixed ultrasonic probe devices that operate in the low 20–30 kHz range are best in disintegrating the small stones and pneumatic impact probes that deliver very high energy but at lower frequencies of 5–20 impacts per second.

Another technique uses extra-corporeal shock waves for de-bulking calculi. In this instance, a patient is subjected to shock waves with the shock waves passing through a patient's skin which causes bruising and is not acceptable for pregnant women and is slow requiring multiple procedures for large stones. However, there are calculi, which cannot be removed by this technique because of the location, volume or composition, or health of patient.

The present invention is directed to a dual probe instrument that combines the higher 20 kHz or more frequency and the high energy shock impacting of the low, for example, less than 1 kHz, frequencies. With the use of concentric probes, a lumen may be established therethrough allowing suction to remove calculi, or stone, debris from a patient.

SUMMARY OF THE INVENTION

A percutaneous surgical instrument for de-bulking calculi or drilling bone in accordance with the present invention generally includes an actuator for generating vibrations at ultrasonic frequencies along with a horn coupled to the actuator for amplifying the actuator vibration.

A fixed probe is attached to the horn for engaging the calculi and introducing ultrasonic frequencies thereto.

A floating probe is provided and disposed concentric to and over the fixed probe with the floating probe being slidable over the fixed probe. A free mass is disposed between the horn and floating probe for oscillating therebetween in response to actuator vibration for causing low frequency impact with the floating probe and calculi. The floating probe could also be on the inside and concentric to the fixed probe on the outside.

A generator may be provided for driving the actuator at desired frequencies, pulse cycles and duty cycles in order to both change the ultrasonic frequency introduced by the fixed probe and the oscillations of the low frequency impacts.

In addition, the fixed probe may include a lumen therethrough for aspiration of disintegrated calculi or bone with the fix probe lumen in communication with a lumen through the horn.

The floating probe may be shorter or longer than the fixed probe and when shorter extends beyond a distal length of the fixed probe during oscillation of the floating probe.

A collar may be provided and fixed to the floating probe at a proximal end thereof for receiving impacts from the free mass. In addition, a housing may be provided for containing the actuator within the housing, including a distal end surrounding the fixed probe and the floating probe at a spaced apart distance from distal ends of the fixed probe and the floating probe.

A biasing spring element is preferably disposed between the collar and the housing distal end for urging the collar into the free mass, compression of the spring occurring during oscillation of the free mass.

The fixed probe and the floating probe may be detachable from the horn and further a plurality of fixed probes and floating probes may be utilized. The plurality of fixed and floating probe preferably include different cutting tips of different design and the generator driving frequency, pulse cycle and duty cycle is preferably selected to optimize the cutting/disintegration effectiveness of a selected fixed and floating probe. Additionally, varying spring rates will affect the impact energy and cycle frequency.

BRIEF DESCRIPTION OF THE DRAWING

The advantages and features of the present invention will be better understood by the following description when considered in conjunction with the accompanying drawings, in which:

FIG. 1 is a cross sectional view of a percutaneous surgical instrument in accordance with the present invention generally showing an actuator for generating vibrations at ultrasonic frequencies, a horn coupled to the actuator for amplifying the actuator vibration, a fixed probe attached to the horn for engaging calculi (not shown), a floating probe disposed concentric to and over the fixed probe, a free mass disposed between the horn and the floating probe for oscillating therebetween and a generator/control for driving the actuator at desired frequencies;

FIG. 2 is an enlarged view of the distal end of the instrument shown in FIG. 1 showing the floating probe in a rearward position exposing a tip of the fixed probe;

FIG. 3 is a cross sectional view similar to FIG. 2 showing the floating probe in a forward position as moved by the free mass against a spring or spring like material with the tip of the floating probe past the tip of the fixed probe; and FIGS. 4a, b, c are enlarged cross sectional views of the tips of the fixed and floating probes showing various configurations for different cutting and disintegration procedures.

DETAILED DESCRIPTION

With reference to FIGS. 1–4c there is shown a percutaneous surgical instrument 10 for de-bulking calculi or drilling/coring bone generally including an actuator 12 for generating vibrations at ultrasonic frequencies which may be formed from a plurality of piezoelectric crystals or magnetostrictive assembly 16 and a back plate 18.

Additionally, a transducer assembly 16 may be configured reduce the capacitive effect of piezo crystals in an insulated stack. This may have an interference affect on other sensitive electrical instruments being operated close by. This is overcome with the placement of insulators 20 at each end and one in the center of the poled crystals 16 to create opposite polarity.

A horn 22 is coupled to the actuator 12 through an abutment 26 and a proximal end 28 of the horn 22. This arrangement provides for amplification of the actuator 12 vibration.

A fixed probe is attached to a distal end 36 of the horn 22 through a fitting 38 for receiving ultrasonic frequencies and engaging a calculi, not shown, for introducing the ultrasonic frequencies thereto.

As hereinabove noted, the fixed probe and actuator operate generally in the 18 kHz frequencies or above for disintegrating small stones, or calculi.

A floating probe 44 is disposed concentric to and over/under the fixed probe 32 and is slidable over the fixed probe.

A fixed and floating probe that may be coated with a lubricating element such as Teflon or a hydrophilic coating.

A collar 48 is attached to a proximal end 52 of the floating probe 44 and provides a means for receiving impacts from a free mass 56 which is disposed between the horn 22 and the floating probe 44 for oscillating therebetween in response to actuator 12 vibration. This causes low frequency impact with the floating probe 32 which in turn transfers the impact forces to the calculi as a distal end 58 of the floating probe 44 is driven pass a distal end 60 of the fixed probe 32.

The induced movement of the free mass due to vibration of the actuator 12 causes forward movement of the free mass 56 against a bias provided by a spring 64. The spring 64 returns the free mass 56 to an original position abutting the distal end 36 of the horn 22. These oscillations are at very low frequencies, for example, less than 1 kHz.

Accordingly, the floating probe 44 operating at these low frequencies efficiently breaks large stones into small pieces and the ultrasonically driven fixed probe 32 then is effective for disintegrating the ruptured calculi into finer particles which then may be aspirated through a lumen through the fixed probe 32 and a lumen through 70 through the horn 22 which communicates with a suction port 74 interconnected with a vacuum source (not shown).

It should be appreciated that the fixed probe 32 and the floating probe 44 shown represent a plurality of fixed and floating probes which may have a variety of tips 80, 82, 84 which may include saw or serrated teeth 88, external bevels 90 or internal bevels 92. Tip 85 is a floating tip that may have the cutting edge finished as 88, 90, or 92. The tips 80, 82, 84 provide examples of various configurations suitable for cutting or drilling calculi, flesh, or bone of different density and configuration.

The fixed probe 32 and the floating probe 44 are preferably adapted for interchangement with the horn 22 either by press fit, as illustrated, or through any other conventional coupling arrangement such as threading, silver solder, or welding.

The fixed probe 32 and floating probe 44 may be made of various materials including grades of plastic. The outside diameter of the floating probe may be 4 mm and for use in lithotripsy, the outside floating probe 44 may be approximately 0–1 mm shorter than the fixed probe 32 and will extend past the fixed probe 32 longitudinally when excited as hereinabove noted.

A generator/controller 96 is provided for driving the actuator 12 at desired frequencies. The generator provides for varying the pulse frequencies to fit the type and size of stone or other material to assure the most expedient and efficient disintegration. In fact, the actuator 12 is driven at various frequencies, pulse cycles and duty cycles to maximize efficiency of the instrument 10.

The actuator 12 may be driven by the generator 96 at various frequencies, pulse cycle frequency and duty cycles to maximize the efficiency of each of the cutting tips 80, 82, 84, for example, A housing 100 is provided for containing the actuator 12 and it includes a distal end 102 surrounding the fixed probe 32 and floating probe 44 from the distal ends 60, 58 of the fixed and floating probes 32 and 44 at a distance. An interior surface 104 provides a means of support for the spring 64 which provides for the biasing element between the collar 48 and the housing distal end 102 as hereinabove noted.

Although there has been hereinabove described a specific dual probe in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. A percutaneous surgical instrument for de-bulking calculi or drilling bone, the instrument comprising:

an actuator for generating vibrations at ultrasonic frequencies;

a horn coupled to said actuator for amplifying the actuator vibration;

a fixed probe attached to said horn for engaging the calculi and introducing the ultrasonic frequencies thereto;

a floating probe disposed concentric to and over said fixed probe, said floating probe being slidable over said fixed probe;

a free mass, disposed between said horn and said floating probe for oscillating therebetween, in response to actuator vibration, for causing low frequency impact with the calculi.

2. The instrument according to claim 1 wherein said fixed probe includes a lumen therethrough for aspiration of disintegrated calculi or bone.

3. The instrument according to claim 2 wherein said horn includes a lumen therethrough in communication with the fixed probe lumen.

4. The instrument according to claim 1 wherein said floating probe is longer than said fixed probe.

5. The instrument according to claim 1 wherein said floating probe is shorter than said fixed probe and extends beyond a distal end of said fixed probe during oscillation of said floating probe.

6. The instrument according to claim 1 further comprising a collar, fixed to said floating probe at a proximal end thereof, for receiving impacts from said free mass.

7. The instrument according to claim 1 further comprising a generator for driving said actuator at desired frequencies, pulse cycles and duty cycles in order to both change the ultrasonic frequency introduced by said fixed probe and the oscillations of the low frequency impacts.

8. The instrument according to claim 6 further comprising a housing for containing said actuator and having a distal end surrounding said fixed probe and said floating probe at a spaced apart distance from distal ends of said fixed probe and said floating probe.

9. The instrument according to claim 8 further comprising a biasing element disposed between said collar and the housing distal end.

10. The instrument according to claim 1 wherein said fixed probe and floating probe are detachable from said horn.

11. The instrument according to claim 10 further comprising a plurality of fixed probes and floating probes.

12. The instrument according to claim 10 wherein said plurality of fixed and floating probes include cutting tips of different designs.

13. The instrument according to claim 1 further comprising a generator for driving said actuator at desired frequencies, pulse cycles and duty cycles in order to both change the ultrasonic frequency introduced by said fixed probe and the oscillations of the low frequency impacts depending on a selected one of the plurality of fixed probe and a selected one of the plurality of floating probes.

14. A percutaneous surgical instrument for de-bulking calculi or drilling bone, the instrument comprising:

an actuator for generating vibrations at ultrasonic frequencies;

a horn coupled to said actuator for amplifying the actuator vibration;

a fixed probe attached to said horn for engaging the calculi or bone and introducing the ultrasonic frequencies thereto, said fixed probe having a lumen therethrough for aspiration of disintegrated calculi or bone;

a floating probe disposed concentric to and over said fixed probe, said floating probe being slidable over said fixed probe;

a free mass, disposed between said horn and said floating probe for oscillating therebetween, in response to actuator vibration, for causing low frequency impact with the calculi or bone.

15. The instrument according to claim 14 wherein said horn includes a lumen therethrough in communication with the fixed probe lumen.

16. The instrument according to claim 14 wherein said floating probe is longer than said fixed probe.

17. The instrument according to claim 14 wherein said floating probe is shorter than said fixed probe and extends beyond a distal end of said fixed probe during oscillation of said floating probe.

18. The instrument according to claim 14 further comprising a collar, fixed to said floating probe at a proximal end thereof for receiving impacts from said free mass.

19. The instrument according to claim 14 further comprising a generator for driving said actuator at desired frequencies, probe cycles and duty cycles in order to both change the ultrasonic frequency introduced by said fixed probe and the oscillations of the low frequency impacts.

20. The instrument according to claim 19 further comprising a housing for containing said actuator and having a distal end surrounding said fixed probe and said floating probe at a spaced apart distance from distal end of said fixed probe and said floating probe.

21. The instrument according to claim 20 further comprising a biasing element disposed between said collar and the housing distal end.

22. The instrument according to claim 14 wherein said fixed probe and floating probe are detachable from said horn.

23. The instrument according to claim 22 further comprising a plurality of fixed probes and floating probes.

24. The instrument according to claim 23 further comprising a generator for driving said actuator at desired frequencies, pulse cycles and duty cycles in order to both change the ultrasonic frequency introduced by said fixed probe and the oscillations of the low frequency impacts depending on a selected one of the plurality of fixed probe and a selected one of the plurality of floating probes.

25. A percutaneous surgical instrument for de-bulking calculi or drilling bone, the instrument comprising:

an actuator for generating vibrations at ultrasonic frequencies;

a horn coupled to said actuator for amplifying the actuator vibration;

a fixed probe attached to said horn for engaging the calculi and introducing the ultrasonic frequencies thereto;

a floating probe disposed concentric to and within said fixed probe, said floating probe being slidable within said fixed probe;

a free mass, disposed between said horn and said floating probe for oscillating therebetween, in response to actuator vibration, for causing low frequency impact with the calculi.

26. The instrument according to claim 1 wherein the actuator is configured with unpoled insulators for reducing capacitive effect on the horn.

* * * * *